United States Patent [19]

McAndless et al.

[11] Patent Number: 4,976,924
[45] Date of Patent: Dec. 11, 1990

[54] AUTOMATED THERMAL DESORPTION UNIT

[75] Inventors: John M. McAndless; James R. Hancock, both of Alberta; Donald B. Barnett, Saskatchewan; Orville J. Olm, Saskatchewan; Terry J. A. Locke, Saskatchewan; John Maybank, Saskatchewan, all of Canada

[73] Assignee: The Queen in Right of Canada as represented by the Minister of National Defence, Ottawa, Canada

[21] Appl. No.: 184,808

[22] Filed: Apr. 22, 1988

[51] Int. Cl.$^5$ .............................................. G01N 1/10
[52] U.S. Cl. .................................... 422/99; 422/64; 422/65; 422/67; 422/70; 422/89; 422/104
[58] Field of Search ...................... 422/63, 64, 65, 66, 422/67, 70, 88, 89, 104, 99

[56] References Cited

U.S. PATENT DOCUMENTS

| | | | |
|---|---|---|---|
| 3,812,597 | 5/1974 | Perilhou et al. | 422/65 X |
| 3,859,051 | 1/1975 | Natelson | 422/65 X |
| 4,168,955 | 9/1979 | Allington | 422/64 X |
| 4,387,076 | 6/1983 | Cabrera et al. | 422/66 X |
| 4,595,562 | 6/1986 | Liston et al. | 422/63 X |
| 4,681,741 | 7/1987 | Haraway | 422/63 X |
| 4,693,867 | 9/1987 | Commarmot et al. | 422/64 |
| 4,711,764 | 12/1987 | Good | 422/65 |
| 4,861,553 | 8/1989 | Mawhirt et al. | 422/65 |

Primary Examiner—Robert J. Warden
Assistant Examiner—Lynn M. Kummert
Attorney, Agent, or Firm—Roylance, Abrams, Berdo & Goodman

[57] ABSTRACT

A thermal desorption unit includes a base plate and a pair of spaced apart plates arranged perpendicularly to the base plate and positioned to hold a magazine of tubes between the spaced apart plates. The unit includes apparatus for selectively extracting, handling, heating, and reinserting a tube from the magazine. The tubes are heated to drive off the contents and flushed to clean the inside of the tubes.

8 Claims, 5 Drawing Sheets

AUTOMATED THERMAL DESORPTION UNIT

FIELD OF INVENTION

The present invention relates to an automated thermal desorption unit for retrieving gaseous samples from an air sampling magazine as fully described in U.S. patent application Ser. No. 184,810 filed on Apr. 22, 1988, now U.S. Pat. No. 4,869,117 and entitled "Polymer Packed Mini-Tube Vapour Sampling System", and naming the same inventors as named in the instant application.

BACKGROUND OF THE INVENTION

The trapping and collection of airborne contaminants in the form of gases, vapours, or the like is of importance in a number of fields. For example, contaminants may be collected to determine the downwind spread of herbicides or pesticides from a crop spraying operation to determine industrial compliance with air quality standards, to monitor the workplace air quality, or to control the use of toxic materials and to monitor and identify toxic substances released during military encounters.

The current techniques for collecting air samples are:
a. by using liquid filled impingers or bubblers. Air is drawn (bubbled) through the liquid which partially, or completely, dissolves the contaminants and thus removes them from the air stream. The solution is subsequently analysed by injection into, e.g., a gas chromatograph;
b. by using tubes packed with a solid porous adsorbant. The solid material retains contaminants by, e.g., physical inclusion in pores or electrostatic attraction at active polar sites on the surface of the solid when air is drawn through the tubes. The solid material is subsequently solvent extracted and the extract is analysed, or the material is heated to thermally desorb the trapped contaminants into an appropriate apparatus for analysis;
c. by collecting sample volumes of the air in suitable containers such as large bags or gas syringes. The air is withdrawn from the collection container using a small gas-tight syringe and injected into an analysis apparatus;
d. by drawing air continuously through analysers which monitor contaminant concentration in real time or near real time.

The disadvantages of the prior art have been overcome as regards the sampling apparatus by, the system disclosed in the companion application referred to above, utilizing a cylindrical magazine containing a large number of mini-tubes prepacked with an absorbant material in which samples of the gas are collected. The object of this invention is to provide an automated desorption unit for removing the gas from the mini-tubes within a magazine and leaving the mini-tubes in a clean condition within the magazine ready for reuse in the sampling apparatus.

SUMMARY OF THE INVENTION

According to the present invention there is therefore provided a thermal desorption unit into which a magazine containing mini-tubes can be placed. Each mini-tube is selectively withdrawn automatically from the magazine, the sample of gas is taken from the mini-tube by heating, the mini-tube is flushed with heated air to cleanse the absorption material within the mini-tube and the inner walls of the tube, and the tube replaced within the magazine. The desorption unit is automated so that it is merely necessary to place the magazine within the unit, activate the unit and it will then proceed to retrieve every mini-tube sample, have each sample analyzed and eventually switch itself off when all of the samples have been retrieved and analysed leaving a full magazine with completely clean mini-tubes therein. The operator will then remove the magazine from the unit for use in a sampling apparatus of the type disclosed in the copending application referred to above.

More specifically the thermal desorption unit consists of a base plate, a pair of spaced apart plates upstanding from the base plate, means for locating a cylindrical magazine of mini-tubes between the plates, means for selectively extracting a tube from the magazine, means for heating the tube to drive-off the gas retained therein, means for cleaning the tube with hot air, means for inserting the tube within the magazine and means for moving the tubes within the magazine to position a next tube for withdrawal.

BRIEF DESCRIPTION OF THE DRAWINGS

In the accompanying drawings which illustrate an exemplary embodiment of the invention.

DETAILED DESCRIPTION

Figure 1:
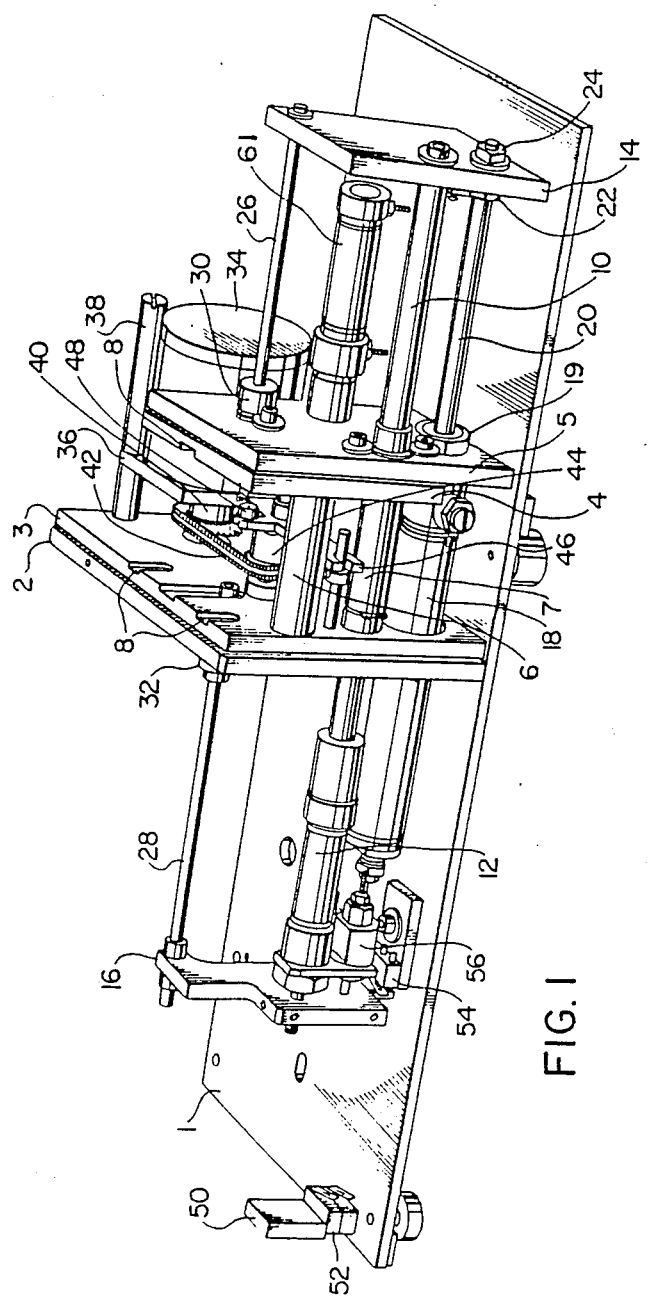
FIG. 1a is a perspective view of the magazine holding part of the desorption unit.

Referring to the drawings and specifically to FIG. 1, this part of the mechanism consists of a baseplate (1) having a bulkhead (2) secured thereto by welding or by a suitable type of screw fastener, or the like. Secured to the bulkhead (2) by tap bolts, or the like, is an index plate (3). A second plate (5) is positioned upon the bulkhead (2) and a second indexer plate (4) is secured to plate (5) by tap bolts, or the like. A spacer (6) prevents the indexer plates (3) and (4), from approaching to a distance less than the thickness of a cylindrical magazine of the type disclosed in the copending application referred to previously. A piston and cylinder unit (61) is secured between plates (2) and (5) to move plate (5) relative to plate (2) to grip the magazine when in the indexed position. Slots (8) are formed in plates (3) and (4) to accommodate mating protrusions on the magazine holding the samples of gases to so position the magazine accurately within the unit. A sleeve bushing (7) is secured by welding to index plate (3) and has a slide rod (10) passing there through. The slide rod (10) is adjustable in length by a pneumatically operated extension cylinder (12). At respective ends of the slide rod (10) there are secured slide plates (14) and (16) which can move in unison relative to index plates (3) and (4). The slide rod (10) is secured to the end plates by threaded bores and tap bolts or threaded ends and nuts.

In order to activate the slide rod (10) and end slide plates (14) and (16), a pneumatically operated cylinder and piston arrangement (18) is utilized, the cylinder being secured to plate (5) by a threaded end and a nut (19) and the piston being secured through a piston rod (20) to slide plate (14) by a threaded end and two nuts (22) and (24). Secured respectively to the slide plates (14) and (16) are insert rods (26) and (28) which are secured by tap bolts, or threaded portions and nuts, to the slide plates (14) and (16) at one end of each rod thereof, and at the other end are slidingly supported in bearings (30) and (32) which are secured respectively to plates (2) and (5).

In order to move the tubes sequentially within the magazine, there is an indexing mechanism consisting of a prime mover such as an electric motor (34) which is secured through a support plate (36) secured to a rod (38) extending from plates (2) and (3). The motor (34) has a drive sprocket (40) upon its shaft which drives a drive belt (42) to rotate a crank assembly (44). Any other drive mechanism such as a belt drive, or the like, can also be used. The crank assembly is secured by a known mechanical method to a reciprocating lever mechanism (46) which has a pawl (48) which contacts the magazine when it is required to move the tubes within the magazine by a distance to align a next tube. Note that when a tube is aligned within the magazine in its operative position, the cylinder (12) will be actuated, the slide rods (26) and (28) will be moved slightly closer towards each other to grip the specific tube between them, and the cylinder and piston assembly (18) will be actuated to move the slide plates (14) and (16) from right to left as shown in FIG. 1 to thus withdraw the tube between the ends of the rods (26) and (28), from the canister, for processing. Varous limit switches and limit yalves (50) (52) (54) and (56) are utilized to control the operation, these being interconnected in any well known manner which is not part of this invention.

Figure 2:
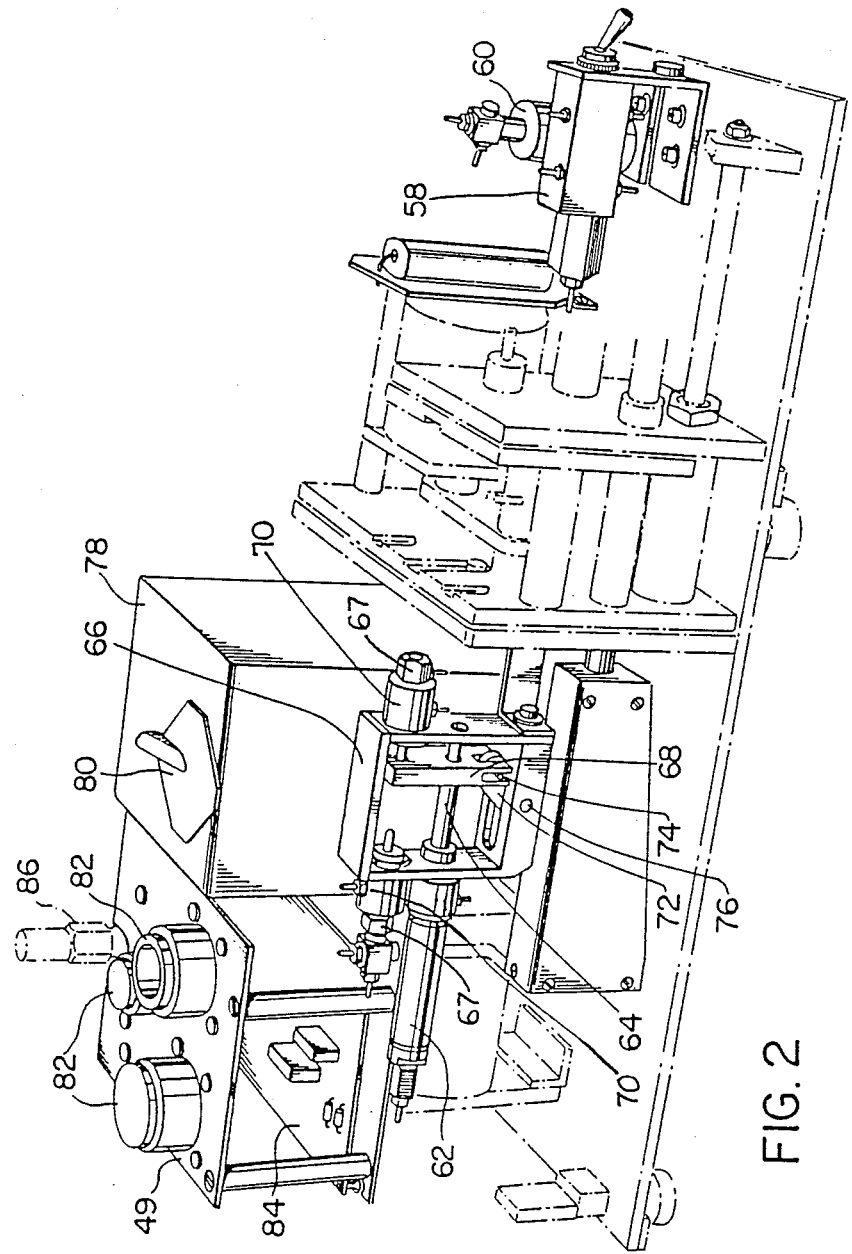
FIG. 2 is a perspective view of components of the desorption unit which activate mechanism for handling a mini-tube after its removal from the magazine.

Referring to FIG. 2 a switch (58) together with a solenoid valve (60) are used to activate cylinder (61) (shown in FIG. 1) to move index plates (3) and (4) to a clamping position upon the magazine.

An operating mechanism to handle a tube removed from the magazine is partly shown in FIG. 2 and consists of a pneumatic cylinder (62) operating a piston rod (64) and held within a substantially square, rigid, box frame (66). A cross head (68) is secured by a threaded end to the piston rod and can reciprocate within the frame (66), under the control of limit switches and valves (67) and (70). The lower end of the cross head (68) is arranged with slots to accommodate the end of a lever (72) having a pin (74) there through. The lever (72) is pivoted about an axle (76) which is rotatably held within the base of frame (66). The axle (76) extends behind the frame (66) and passes into the box (78) which is the housing for the thermal mechanism for retrieving the gaseous material from the tubes. A cover hatch (80) enables access to the inside of the housing (78).

Connectors (82) are for electrical cables for power and control systems which includes feed circuit board (84) which provides power to the various components in the unit.

Figure 3:
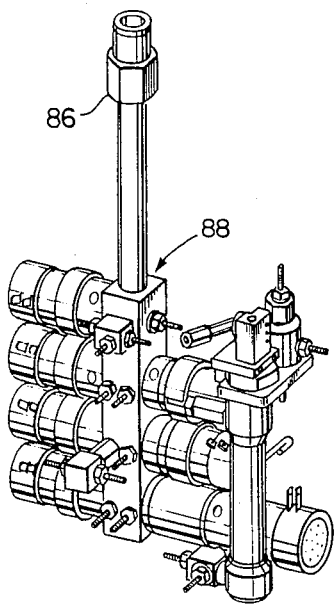
FIG. 3 is a perspective view of an air inlet manifold having attached thereto various solenoid valves associated with the desorption unit.

Pipe (86) is also shown in FIG. 3 and is an air pipe which feeds a manifold (88) from which various solenoid valves control air to the various cylinders and valves throughout the unit.

Figure 4:
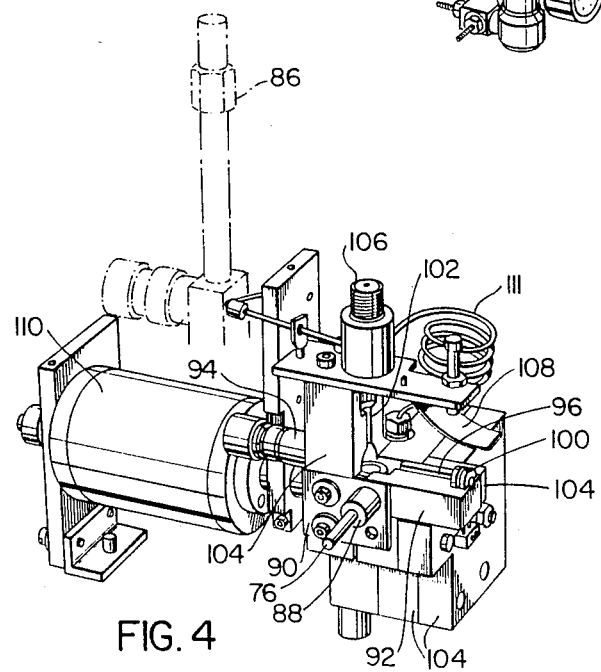
FIG. 4 is a perspective view of the mini tube handling mechanism.

FIG. 4 again shows the pipe (86) and its association with mechanism for retrieving the gas from a tube, this mechanism being inside the housing (78). Shaft (76) as shown in FIG. 2 extends to the mechanism in FIG. 4 and is secured through a bearing (88) secured to a plate (90). A tilting block (92) is rigidly secured to the end of shaft (76) so that it can rotate from the position shown in FIG. 4 ninety degrees counter clockwise. The sliding rod (28) shown in FIG. 1 passes through bearing (94) and can deposit a tube in groove (96). The block (92) can then be rotated through the ninety degrees so positioning the tube between a lower seal (98) and an upper seal (100). The tube will then be held between groove (96) and groove (102). Groove (102) is formed within a block (104) which is heated by heating elements contained within thermal block (104) so that the gaseous material can be driven from the tube held between blocks (92) and (104). The gaseous material is then driven through a connector (106) to the analysing equipment. A tube guide (108) is utilized to hold a tube within the operating position during rapid movement of the block (92). After the gaseous material has been driven from the tube, air is accepted from inlet (86), is heated and purges and cleans the inside of the tube so that it is ready for use in collecting more gaseous material. An inlet valve (110) controls the flow of gaseous material from the tube and air for flushing the tube and cleansing it. A coil (111) is used to cool the retrieved gaseous material before passing it on to an analyser.

Figure 5:
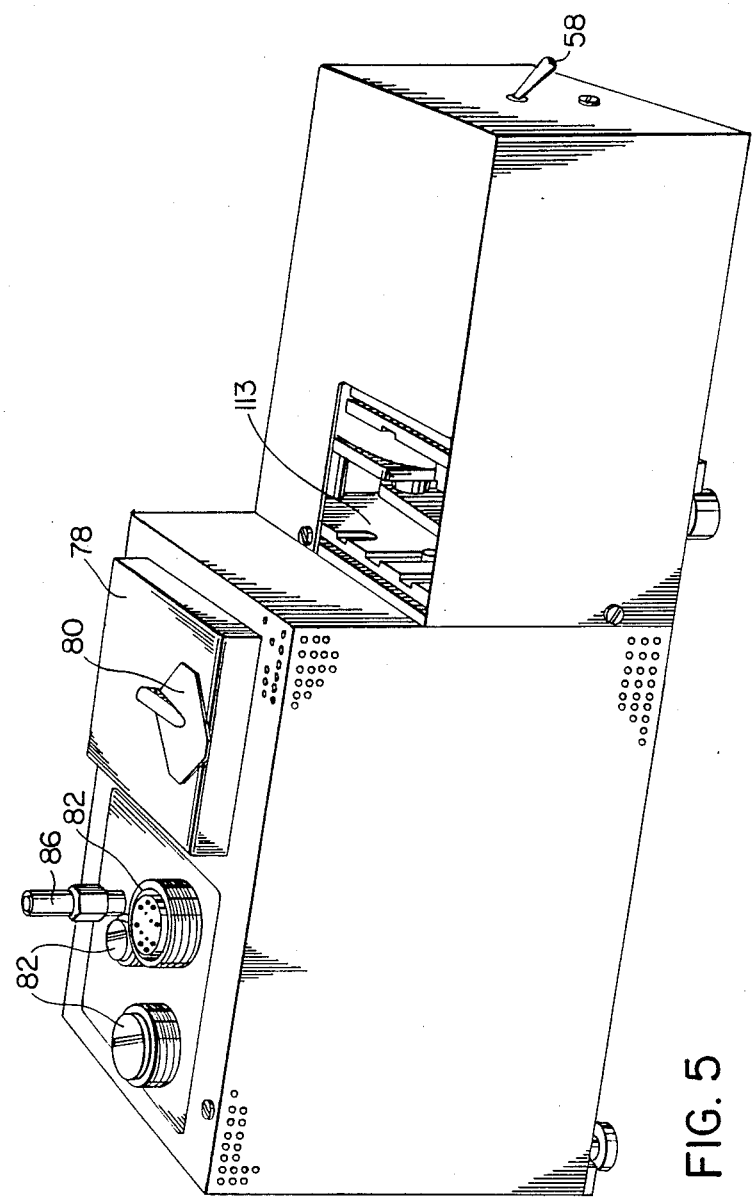
FIG. 5 is a perspective view of the outside of the desorption unit in enclosed operational attitude.

Referring specifically to FIG. 5 the complete desorption unit is shown with an outer enclosure, the indexer clamping switch (58) protruding from the front of the enclosure, and aperture (113) being in the top of the enclosure for accepting a magazine containing the mini tube samples. The top of the thermal housing (78) protrudes from the top of the enclosure and has hatch (80) easily operable to view a tube being manipulated within the thermal handling area of the unit. The air inlet (86) and the connectors (82) for electrical leads also protrude from the top of the enclosure.

Figure 6:
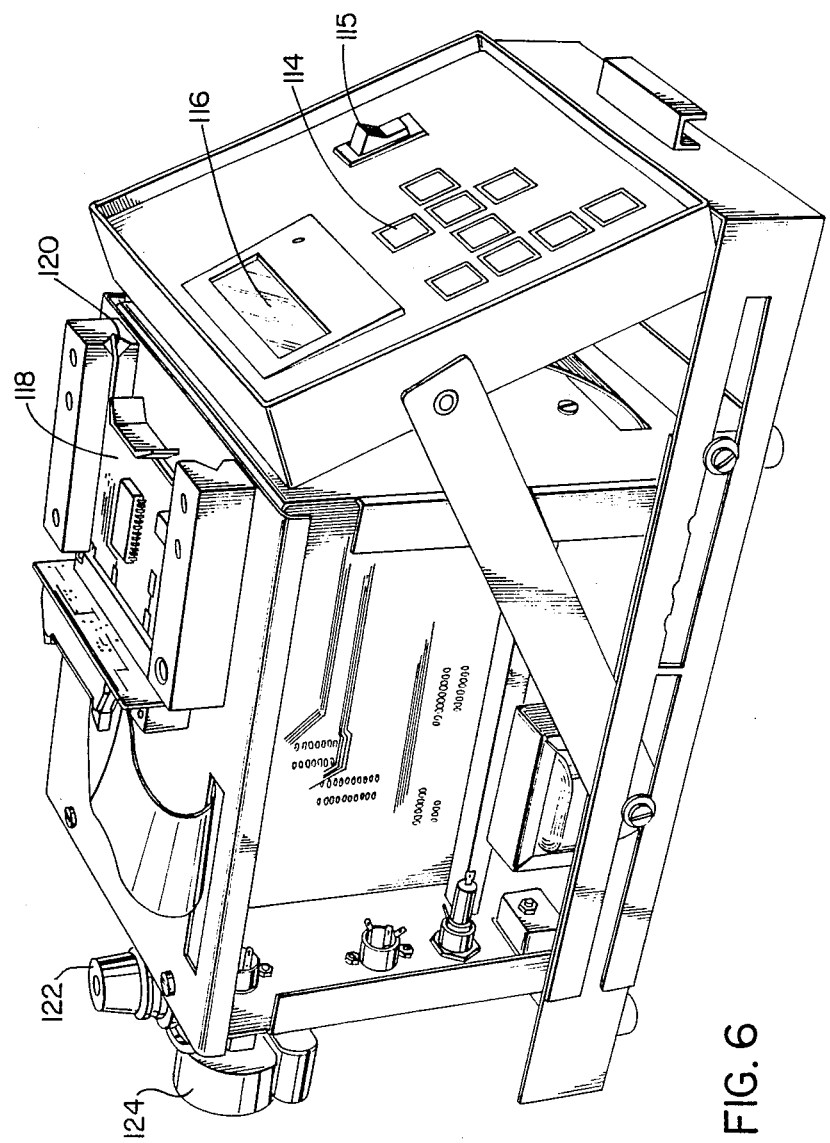
FIG. 6 is a perspective view of the controller of the desorption unit.

The operating console is shown in FIG. 6 and consists of a set of push buttons (114), an on/off switch (115), and a display screen (116). A program card (118) is held in a slot (120) at the top surface of the unit and this program card can easily be replaced by a differently programmed card to achieve different operating sequences of the desorption unit. An air pressure regulator (122) is also associated with this control unit and has a pressure guage (124) for monitoring the air pressure within the desorption unit. The controller unit is not being described in detail as it is merely an electronic programmable control for a mechanical valve system as used in the desorption unit.

It is thus seen that a desorption unit has been disclosed which is self-contained and which handles mini-tubes from the magazine as disclosed in the copending previously referred to application and which both removes the gaseous material from the mini-tubes and leaves the mini-tubes in reusable condition without any other process having been required upon the tubes.

We claim:

1. A thermal desorption unit, comprising:
   a base plate;
   a pair of spaced apart plates arranged perpendicularly to said base plate;
   locating means for accomodating a cylindrical magazine of tubes between said spaced apart plates;
   extraction means for selectively extracting a tube from the magazine;
   manipulator means for handling the extracted tube;

heating means for removing contents of the extracted tube;

flushing means for cleaning the extracted tube;

reinsertion means for replacing the extracted tube within the magazine; and positioner means for moving the tubes within the magazine for selective retrieval;

whereby said unit can accept a magazine of tubes containing samples and produce a magazine of clean tubes ready for reuse.

2. The unit of claim 1, wherein said locating means comprises a pair of index plates each having a top edge secured to a respective one of said spaced apart plates, said index plates having grooves extending downwards from said top edges, said grooves being constructed to accept locating bosses on the magazine.

3. The unit of claim 2, wherein one of said index plates is movable towards said other index plate to grip a magazine therebetween.

4. The unit of claim 3, wherein a piston and cylinder are used to move said index plate.

5. The unit of claim 1, wherein said extraction means includes a sliding rod parallel to said base plate;

a sleeve bushing extending between said spaced apart plates supporting said sliding rod;

slide plates secured at opposite ends of said sliding rod;

a cylinder extending parallel to said sliding rod, secured to one of said spaced apart plates;

a piston rod extending from said cylinder and secured to one of said slide plates so that both of said slide plates can be moved in unison;

two axially aligned insert rods having ends; and bearings, on each said spaced apart plate, for supporting each said insert rod between one of said slide plates and adjacent spaced apart plate, said ends of said axially aligned rods being positioned to straddle the ends of an extractable tube within a magazine.

6. The unit of claim 1, wherein said positioner means comprises a prime mover secured to one of said spaced apart plates;

a selectively driven lever and cam means for contacting a magazine internally to selectively move the tubes to a position from which the tubes can be extracted.

7. The unit of claim 1, wherein said manipulator means includes a first horizontal block having a semicircular groove therein, said first block having two ends with one of said ends serving as a pivot point; and a second fixed vertical block having a lower end and a semicircular groove therein, said second block having means defining a sealable opening at said lower end thereof and said first block having means defining a sealable opening at the non-pivoting end thereof such that an extracted tube can be placed upon said semicircular groove in said first block and pivoted to meet said second block wherein the tube fits between said sealable openings so that the contents of the tube can be retrieved.

8. The unit of claim 7, wherein said heating means and flushing means include a source of heated air for purging and cleaning the extracted tube.

* * * * *